United States Patent
Enomoto

(10) Patent No.: US 9,618,844 B2
(45) Date of Patent: Apr. 11, 2017

(54) REAGENT AND COMPOSITION OF RESIST

(71) Applicant: TOYO GOSEI CO., LTD., Ichikawa-shi, Chiba (JP)

(72) Inventor: Satoshi Enomoto, Kamagaya (JP)

(73) Assignees: Toyo Gosei Co., Ltd., Ichikawa-shi, Chiba (JP); Osaka University, Suita-shi, Osaka (JP)

( * ) Notice: Subject to any disclaimer, the term of this patent is extended or adjusted under 35 U.S.C. 154(b) by 0 days.

(21) Appl. No.: 14/891,293

(22) PCT Filed: May 13, 2014

(86) PCT No.: PCT/JP2014/002531
§ 371 (c)(1),
(2) Date: Nov. 13, 2015

(87) PCT Pub. No.: WO2014/185065
PCT Pub. Date: Nov. 20, 2014

(65) Prior Publication Data
US 2016/0070165 A1     Mar. 10, 2016

Related U.S. Application Data

(60) Provisional application No. 61/822,603, filed on May 13, 2013.

(51) Int. Cl.
| | | |
|---|---|---|
| B44C 1/22 | (2006.01) |
| C03C 15/00 | (2006.01) |
| C03C 25/68 | (2006.01) |
| C23F 1/00 | (2006.01) |
| G03F 7/004 | (2006.01) |
| G03F 7/039 | (2006.01) |
| G03F 7/20 | (2006.01) |

(Continued)

(52) U.S. Cl.
CPC ............ *G03F 7/0045* (2013.01); *C07C 33/24* (2013.01); *C07C 35/38* (2013.01); *C07C 35/40* (2013.01); *C07C 49/83* (2013.01); *C07D 219/06* (2013.01); *C07D 309/12* (2013.01); *C07D 311/86* (2013.01); *C07D 335/16* (2013.01); *G03F 7/0392* (2013.01); *G03F 7/0397* (2013.01); *G03F 7/16* (2013.01); *G03F 7/20* (2013.01); *G03F 7/2004* (2013.01); *G03F 7/2037* (2013.01); *G03F 7/2039* (2013.01); *G03F 7/36* (2013.01); *C07C 2103/18* (2013.01)

(58) Field of Classification Search
USPC ............................................. 216/87
See application file for complete search history.

(56) References Cited

U.S. PATENT DOCUMENTS 6,171,755 B1   1/2001   Elian et al.
7,851,252 B2   12/2010  Nealey et al.

FOREIGN PATENT DOCUMENTS

DE   59808434   6/2003
EP   919867     5/2003

(Continued)

OTHER PUBLICATIONS

PCT International Search Report, Aug. 26, 2014, PCT/EP2014/185065.

(Continued)

*Primary Examiner* — Roberts Culbert
(74) *Attorney, Agent, or Firm* — TraskBritt, P.C.

(57) ABSTRACT

Described is a reagent that enhances acid generation of a photoacid generator and a composition containing such reagent.

16 Claims, 1 Drawing Sheet

(51) Int. Cl.
| | | |
|---|---|---|
| *C07C 33/24* | (2006.01) | |
| *C07C 35/38* | (2006.01) | |
| *C07C 35/40* | (2006.01) | |
| *C07C 49/83* | (2006.01) | |
| *C07D 219/06* | (2006.01) | |
| *C07D 309/12* | (2006.01) | |
| *C07D 311/86* | (2006.01) | |
| *C07D 335/16* | (2006.01) | |
| *G03F 7/16* | (2006.01) | |
| *G03F 7/36* | (2006.01) | |

(56) References Cited

FOREIGN PATENT DOCUMENTS

| | | |
|---|---|---|
| JP | 04-165359 | 11/1992 |
| JP | 11231542 | 8/1999 |
| JP | 2013-031125 | 2/2013 |
| JP | 2013-211479 | 2/2013 |
| WO | 2014129556 | 8/2014 |
| WO | 2014185065 | 11/2014 |

OTHER PUBLICATIONS

Seiji Nagahara et al., Methods to Improve Radiation Sensitivity of Chemically Amplified Resists by Using Chain Reactions of Acid Generation, In Advances in Resist Technology and Processing XVII, 2000, pp. 386-394, Proceedings of SPIE vol. 3999.

Office Action for co-pending Chinese application number, 201480027633, dated Dec. 15, 2016.

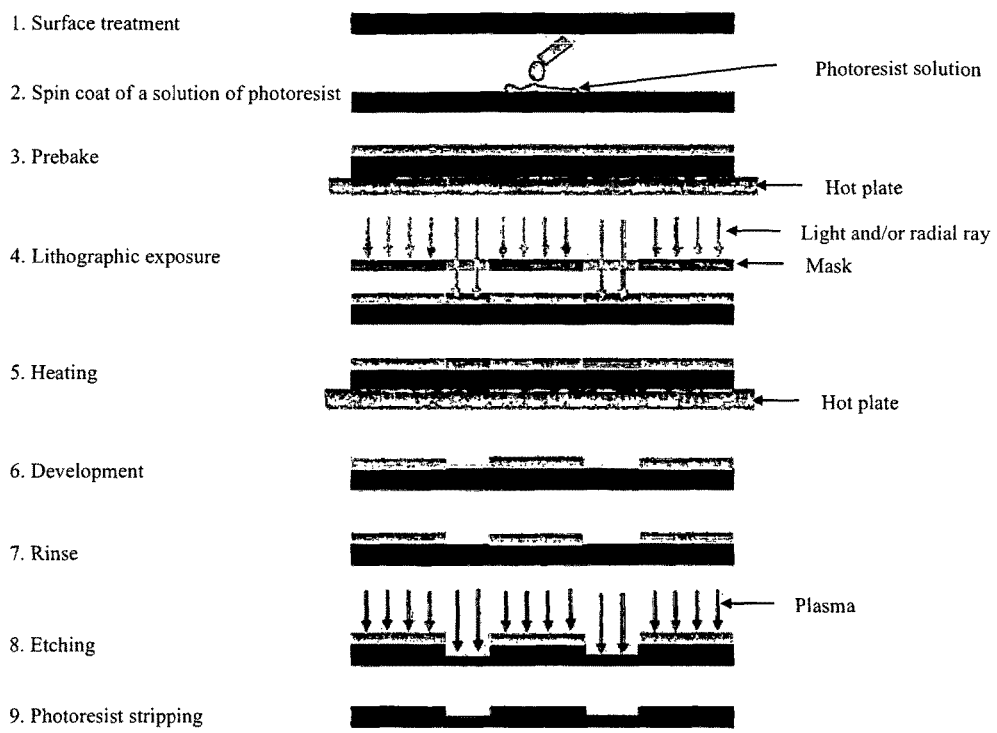

REAGENT AND COMPOSITION OF RESIST

CROSS REFERENCE TO RELATED APPLICATION

This application is a national phase entry under 35 U.S.C. §371 of International Patent Application PCT/JP2014/002531, filed May 13, 2014, designating the United States of America and published in English as International Patent Publication WO 2014/185065 A1 on Nov. 20, 2014, which claims the benefit under Article 8 of the Patent Cooperation Treaty and under 35 U.S.C. §119(e) of U.S. Provisional Patent Application Ser. No. 61/822,603, filed May 13, 2013, the disclosure of each of which is hereby incorporated herein in its entirety by this reference.

TECHNICAL FIELD

Several aspects of the disclosure relate to the fields of chemistry and reagents that enhance acid generation and also to the compositions of resists.

BACKGROUND

Current high-resolution lithographic processes are based on chemically amplified resists (CARs) and are used to pattern features with dimensions less than 100 nm as feature dimensions shrink to below 50 nm.

A method for forming pattern features with dimensions less than 100 nm is disclosed in U.S. Pat. No. 7,851,252 (filed on Feb. 17, 2009), the entire contents of which are incorporated herein by this reference.

BRIEF SUMMARY

Described are reagents that enhance acid generation of an acid generator and compositions of photoresists. Typically, such a reagent assists the generation of a Brönsted acid. Furthermore, such a reagent can apply to the generation of a Lewis acid. Typically, such a reagent generates an intermediate having a reducing character.

Examples of such reagents are bisaryl ketones, arylalkyl ketones, bisarylmethyl halides, benzoins, carbazoles, alkoxy (or aryloxy) benzophenone, alkoxy (or aryloxy) methyl-naphthalene, and reagents containing at least one benzyl group.

In certain embodiments, the reagent is characterized in that, when energy is directly or indirectly applied to an acceptor other than the reagent, the reagent generates an intermediate by receiving energy from the excited acceptor or reacting with the excited acceptor or reactive chemical species generated from the acceptor, and the intermediate enhances generation of acid from a precursor.

In certain embodiments, the reagent is characterized in that, when energy is directly or indirectly applied to the reagent, an intermediate is generated from the reagent, and the intermediate enhances generation of acid from a precursor.

In certain embodiments, the intermediate may have a reducing character. In certain embodiments, the intermediate may be a radical, such as a ketyl radical.

In certain embodiments, the intermediate discharges at least one of a hydrogen atom and a hydrogen ion that has reducing characteristics.

In certain embodiments, the energy includes irradiation with a light, such as an extreme ultraviolet light or a light having a wavelength less than or equal to 15 nm. The energy may include exposure to particle ray such as electron beam.

As an example, the composition of photoresist can be applied to the manufacture of electronic devices, such as, semiconductor devices and electro optical devices.

A reagent in certain embodiments relating to an aspect of this disclosure is characterized in that a feed of energy to the reagent or to an acceptor receiving the energy generates an intermediate from the reagent, and the intermediate enhances a generation of chemical species acid from a precursor such as acid and base.

It is preferred that the intermediate has a reducing character or an electron donor character. A photoacid generator may easily generate acid or base by receiving an electron from the intermediate.

It is preferred that the intermediate is a reactive intermediate such as a radical.

It is preferred that the intermediate discharges at least one of a hydrogen atom and a hydrogen ion that have reducing characteristics.

It is preferred that the intermediate is a ketyl radical. Such ketyl radical can be a stabilized aryl group and the reagent having at least one aryl group can easily form such ketyl radical.

It is preferred that the feed of the energy is carried out by irradiation with a light or exposure to particle ray.

It is preferred that the feed of the energy is carried out by an irradiation of the reagent with at least one of a light of which the wavelength is equal to or shorter than 15 nm and an electron beam. The feed of energy carried out by the irradiation with such light or electron beam enables formation of pattern with ultrafine structure.

A composition in certain embodiments relating to an aspect of this disclosure comprises any one of the reagents above and a first compound that functions as a generation source of acid.

It is preferred that the composition further comprises a second compound that has a bond cleavable by chemical species such as acid and base.

A composition in certain embodiments relating to an aspect of this disclosure comprises a reagent represented by formula (I) and a first compound that functions as a generation source of acid.

It is preferred that $R^1$ is a hydrogen atom; $R^2$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom; and $R^3$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom.

A composition in certain embodiments relating to an aspect of this disclosure comprises a reagent and a first compound that generates acid by accepting energy, accepting an electron or at least one hydrogen atom.

With regard to the composition, it is preferred that the reagent comprises a hydroxyl group and a first cyclic moiety that contains a carbon atom bonded to the hydroxyl group and a hydrogen atom.

With regard to the composition, it is preferred that the reagent further comprises a second cyclic moiety, and the first cyclic moiety containing at least two atoms, which are also contained in the second cyclic moiety.

With regard to the composition, it is preferred that the reagent further comprises a third cyclic moiety, and the first cyclic moiety contains at least two atoms that are also contained in the third cyclic moiety.

With regard to the composition, it is preferred that the first cyclic moiety is either a six-membered ring or a five-membered ring.

With regard to the composition, it is preferred that the second cyclic moiety is an aromatic group.

A composition in certain embodiments relating to an aspect of this disclosure comprises a reagent represented by formula (II) and a first compound that generates acid by accepting energy, accepting an electron or at least one hydrogen atom.

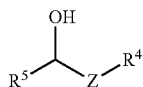

(II)

With regard to the composition, it is preferred that: Z is a carbonyl group, a methylene group, an alkoxymethylene, an aryloxymethylene, or a hydroxymethylene; $R^4$ is an aryl group or an aryl group containing an aromatic group and a substituent on the aromatic group containing at least one atom other than carbon atom and hydrogen atom; and $R^5$ is a hydrogen atom, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom.

With regard to the composition, it is preferred that the first compound is an organic salt containing an iodonium ion or a sulfonium ion.

With regard to the reagent, it is preferred that the intermediate is generated by abstracting a hydrogen atom from the reagent.

With regard to the reagent, it is preferred that a difference between at least one of a first oxidation potential of a ground state and a second oxidation potential of an excited state of the intermediate and at least one of a first reduction potential of the ground state and a second reduction potential of the excited state of the precursor is equal to or greater than 0.10 eV.

With regard to the reagent, it is preferred that the first reduction potential is lower than at least one of the first oxidation potential and the second oxidation potential.

With regard to the reagent, it is preferred that the intermediate has reducing character.

With regard to the reagent, it is preferred that the intermediate is a radical.

With regard to the reagent, it is preferred that the intermediate discharge at least one of a hydrogen atom and a hydrogen ion that have reducing characteristics.

With regard to the reagent, it is preferred that the intermediate is a ketyl radical.

With regard to the reagent, it is preferred that the feed of the energy is carried out by irradiation of the reagent with a light.

With regard to the reagent, it is preferred that the feed of the energy is carried out by an irradiation of the reagent with at least one of a light of which the wavelength is equal to or less than 15 nm and an electron beam.

With regard to the reagent, it is preferred that the intermediate is generated by having a hydrogen atom of the reagent abstracted.

A method for manufacturing a device in certain embodiments relating to an aspect of this disclosure, the method comprises applying a solution of any one of the compositions to a substrate such that a film including the composition is formed on the substrate, and irradiating the film with at least one of an electromagnetic ray and a particle ray such that a first portion of the film is irradiated with the at least one of the electromagnetic ray and the particle ray while a second portion of the film is not irradiated with the at least one of the electromagnetic ray and the particle ray.

With regard to the method, it is preferred that the method further comprises removing the first portion.

With regard to the method, it is preferred that the method further comprises etching the substrate such that a third portion of the substrate on which the first portion has been present is etched.

With regard to the method, it is preferred that the irradiating of the film is carried out using at least one of an EUV light and an electron beam.

A reagent in certain embodiments relating to an aspect of this disclosure is characterized in that, when energy is directly or indirectly applied to the reagent, an intermediate is generated from the reagent and the intermediate enhances generation of acid from a precursor.

With regard to the reagent, it is preferred that the intermediate has a reducing character.

With regard to the reagent, it is preferred that the intermediate is a radical.

With regard to the reagent, it is preferred that the intermediate is a ketyl radical.

With regard to the reagent, it is preferred that the intermediate discharges at least one of a hydrogen atom and a hydrogen ion that has reducing characteristics.

With regard to the reagent, it is preferred that the energy includes irradiation with light.

With regard to the reagent, it is preferred that the light has a wavelength less than or equal to 15 nm.

BRIEF DESCRIPTION OF DRAWINGS

In the drawings, which illustrate what is currently considered to be the best mode for carrying out the disclosure:

FIG. 1 shows fabrication processes of a device, such as, an integrated circuit (IC) utilizing a photoresist including an acid generation enhancer.

DETAILED DESCRIPTION

The disclosure is further described with the aid of the following illustrative Examples.
Experimental Procedures
  Synthesis of 4-hydropyranylacetophenone
  10.0 g of 4-hydroxyacetophenone and 9.89 g of 2H-dihydropyran are dissolved in 80.0 g of methylene chloride. 0.74 g of pyridinium p toluenesulfonate is added to the methylene chloride solution containing 4-hydroxyacetophenone and 2H-dihydropyran. The mixture is stirred at 25 degrees Celsius for 3 hours. Next, the mixture is further stirred after addition of 1% aqueous solution of sodium hydroxide. The organic phase is collected through separation by liquid extraction. 14.4 g of 4-hydropyranylacetophenone is obtained by evaporating solvents from the collected organic phase.

Synthesis of 1-(4-tetrahydropyranylphenyl)ethanol (Example 1)

5.0 g of 4-hydropyranylacetophenone and 0.10 g of potassium hydroxide are dissolved in ethanol. 1.04 g of sodium boronhydride is added to the ethanol solution containing 4-hydropyranylacetophenone and potassium hydroxide. The mixture is added at 25 degrees Celsius for 3 hours. Next, alkali in the mixture is neutralized by 10% aqueous solution of hydrochloric acid. The organic phase is collected through separation by liquid extraction using 100 g of methylene chloride. 4.52 g of 1-(4-tetrahydropyranylphenyl)ethanol is obtained by evaporating solvents from the organic phase.

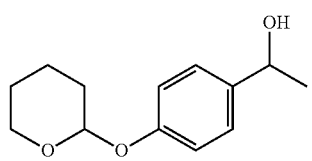

Example 1

Synthesis of Resin A.

A solution containing 5.0 g of alpha-methacryloyloxy-gamma-butylolactone, 6.03 g of 2-methyladamantane-2-methacrylate, and 4.34 g of 3-hydroxyadamantane-1-methacrylate, 0.51 g of dimethyl-2,2'-azobis(2-methylpropionate), and 26.1 g of tetrahydrofuran is prepared. The prepared solution is added for 4 hours to 20.0 g of tetrahydrofuran placed in a flask with stirring and boiling. After the addition of the prepared solution, the mixture is heated to reflux for 2 hours and cooled to room temperature. Addition of the mixture drop-wise to a mixed liquid containing 160 g of hexane and 18 g of tetrahydrofuran (with vigorously stirring) precipitates the copolymer. The copolymer is isolated by filtration. Purification of the copolymer is carried out by vacuum drying following two washings with 70 g of hexane. Thereby, 8.5 g of white powder of the copolymer is obtained.

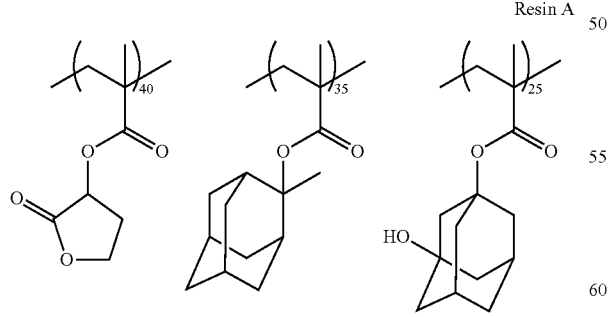

Resin A

Preparation of Samples for Evaluation

Sample 1 is prepared by dissolving 300 mg of resin A, 36.7 mg of 4,4'-di-(t-butyphenyl)iodonium nonafluorobutanesulfonate as a photoacid generator, and 15.0 mg of coumarin 6 as an indicator in 2000 mg of cyclohexanone.

Sample 2 is prepared by dissolving 6.0 mg of 1-(4-tetrahydropyranylphenyl)ethanol, 300 mg of resin A, 36.7 mg of 4,4'-di-(t-butyphenyl)iodonium nonafluorobutanesulfonate as a photoacid generator, and 15.0 mg of coumarin 6 as an indicator in 2000 mg of cyclohexane.

Evaluation of Efficiency of Acid Generation

Films are formed on 4-inch quartz wafers by spin coating of Samples 1 and 2. Each of the films is irradiated with electron beams of which volumes are 0, 10, 20, 30, and 40 myC/cm$^2$ output by an electron beam lithography apparatus. Subsequent to the electron beam exposure, the efficiencies for the films are obtained by plotting absorbances at 534 nm, each of the films of which are assigned to quantities of protonated coumarin 6 generated by the respective volumes of electron beams.

Table 1 shows the relative acid generation efficiencies for the Samples 1 and 2. In Table 1, the acid generation efficiency for the Sample 1 is used as a benchmark. The results shown in Table 1 indicate that the acid generation efficiency is improved by the reduction of the photoacid generator by ketyl radical formed from 1-(4-tetrahydropyranylphenyl)ethanol. In other words, 1-(4-tetrahydropyranylphenyl)ethanol functions as an Acid Generation Enhancer (AGE).

TABLE 1

The relative acid generation efficiencies for Samples 1 and 2.

| | Relative acid-generation efficiency |
|---|---|
| Sample 1 | 1.0 |
| Sample 2 | 1.2 |

Based upon the results, a reactive intermediate having reducing character is considered to enhance the efficiency of acid generation.

Each of Examples 2, 3, 4, and 5 can also be used as an AGE.

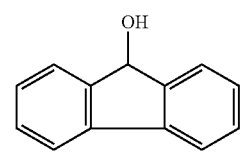

Example 2

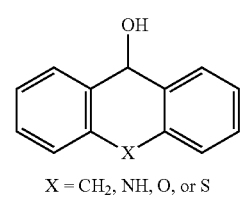

X = CH$_2$, NH, O, or S

Example 3

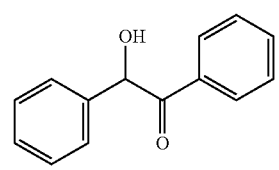

Example 4

Example 5

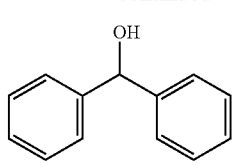

It is preferred that a carbon atom that is bonded to hydroxy group or will be the radical center is bonded to at least one aryl group because such aryl group can stabilize generated radical.

FIG. 1 shows fabrication processes of a device, such as, integrated circuit (IC) using a photoresist including the acid generation enhancer (AGE) obtained by the processes by the above procedures.

A silicon wafer is provided. The surface of the silicon wafer is oxidized by heating the silicon wafer in the presence of oxygen gas.

A solution containing AGE, resin A, and a photoacid generator is applied to the surface of a silicon wafer by spin coating. A film containing AGE, resin A, and the photoacid generator is formed on the surface of the silicon wafer.

An irradiation of the film with an EUV light through a mask is carried out after a prebake of the silicon wafer. The deprotection reaction of resin A is induced by acid generation by photoreaction of the photoacid generator assisted by AGE.

Development of the irradiated film is performed after the prebake.

The irradiated film and the silicon wafer are exposed to a plasma. After that, the remaining film is removed.

An electronic device, such as, an integrated circuit is fabricated utilizing the processes shown in FIG. 1. The deterioration of the device due to the irradiation with a light is suppressed compared to existing photoresists since times for irradiation of the film are shortened.

The invention claimed is:

1. A composition comprising:
   a reagent;
   a first compound that functions as a generation source of acid;
   wherein a feed of an energy to the reagent or to an acceptor for the reagent receiving the energy generates an intermediate from the reagent;
      wherein the intermediate enhances generation of acid from a precursor, wherein the intermediate is a ketyl radical;
   wherein the reagent is selected from the group consisting of a first reagent, a second reagent and a third reagent;
   wherein:
   the first reagent is represented by formula (I);

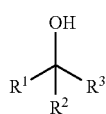
(I)

wherein:
   $R^1$ is a hydrogen atom;
   $R^2$ is a phenyl group, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom; and
   $R^3$ is a hydrogen atom, a phenyl group, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom;
the second reagent is represented by formula (II):

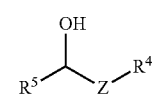
(II)

wherein:
   Z is a carbonyl group, a methylene group, an alkoxymethylene, an aryloxymethylene, or a hydroxymethylene;
   $R^4$ is an aryl group or an aryl group containing an aromatic group and a substituent on the aromatic group containing at least one atom other than carbon atom and hydrogen atom; and
   $R^5$ is a hydrogen atom, a phenyl group, an alkyl carbonyl group, an aryl carbonyl group, an alkyl group, an alkenyl group, an aralkyl group, an alkynyl group, an alkyl group containing a cyclic or poly cyclic moiety, or a substituent containing at least one atom other than carbon atom and hydrogen atom;
   the third reagent includes: a hydroxyl group; and
   a first cyclic moiety that contains a carbon atom bonded to the hydroxyl group and a hydrogen atom.

2. The reagent composition of claim 1, wherein the feed of energy comprises irradiation with light.

3. The composition of claim 1, wherein the feed of energy is carried out by irradiation of the reagent with at least one of light of which the wavelength is less than or equal to 15 nm and an electron beam.

4. The composition of claim 3, further comprising:
   a second compound that has a bond cleavable by acid.

5. The composition of claim 1, wherein:
   the composition further includes a second cyclic moiety, and
   the first cyclic moiety contains at least two atoms that are also contained in the second cyclic moiety.

6. The composition reagent of claim 5, wherein:
   the third reagent further includes a third cyclic moiety, and
   the first cyclic moiety contains at least two atoms that are also contained in the third cyclic moiety.

7. The reagent composition of claim 1, wherein the first cyclic moiety is either a six-membered ring or a five-membered ring.

8. The composition of claim 1, wherein the second cyclic moiety is an aromatic group.

9. The composition of claim 1, wherein the first compound is an organic salt containing an iodonium ion or a sulfonium ion.

10. The composition of claim 1, wherein the intermediate is generated by abstracting a hydrogen atom from the reagent.

11. The composition of claim 1, wherein a difference between at least one of a first oxidation potential of a ground state and a second oxidation potential of an excited state of the intermediate and at least one of a first reduction potential of the ground state and a second reduction potential of the excited state of the precursor is greater than or equal to 0.10 eV.

12. The composition of claim 11, wherein the first reduction potential is lower than at least one of the first oxidation potential and the second oxidation potential.

13. A method of using the composition of claim 1 to manufacture a device, the method comprising:
   applying a solution of the composition to a substrate such that a film including the composition is formed on the substrate; and
   irradiating the film with at least one of an electromagnetic ray and a particle ray such that a first portion of the film is irradiated with the at least one of the electromagnetic ray and the particle ray while a second portion of the film is not irradiated with the at least one of the electromagnetic ray and the particle ray.

14. The method of claim 13, further comprising:
   removing the first portion.

15. The method of claim 14, further comprising:
   etching the substrate such that a third portion of the substrate on which the first portion has been present is etched.

16. The method of claim 13, wherein irradiating the film is carried out using at least one of an EUV light and an electron beam.

* * * * *